(12) United States Patent
Jia et al.

(10) Patent No.: US 11,702,702 B2
(45) Date of Patent: Jul. 18, 2023

(54) SYSTEMS AND METHODS FOR DETECTING GENETIC ALTERATIONS

(71) Applicant: PREDICINE, INC., Hayward, CA (US)

(72) Inventors: Shidong Jia, Palo Alto, CA (US); Pan Du, Dublin, CA (US); Xiaohong Wang, Dublin, CA (US)

(73) Assignee: Predicine, Inc., Hayward, CA (US)

( * ) Notice: Subject to any disclaimer, the term of this patent is extended or adjusted under 35 U.S.C. 154(b) by 754 days.

(21) Appl. No.: 16/093,636

(22) PCT Filed: Apr. 16, 2017

(86) PCT No.: PCT/US2017/027830
§ 371 (c)(1),
(2) Date: Oct. 14, 2018

(87) PCT Pub. No.: WO2017/181161
PCT Pub. Date: Oct. 19, 2017

(65) Prior Publication Data
US 2019/0071732 A1    Mar. 7, 2019

Related U.S. Application Data

(60) Provisional application No. 62/323,547, filed on Apr. 15, 2016, provisional application No. 62/480,288, filed on Mar. 31, 2017.

(51) Int. Cl.
| | |
|---|---|
| C12Q 1/68 | (2018.01) |
| C12Q 1/6886 | (2018.01) |
| C40B 40/06 | (2006.01) |
| C12N 15/10 | (2006.01) |
| C12Q 1/6827 | (2018.01) |
| C12Q 1/6869 | (2018.01) |
| C07H 21/04 | (2006.01) |

(52) U.S. Cl.
CPC ....... *C12Q 1/6886* (2013.01); *C12N 15/1003* (2013.01); *C12Q 1/6827* (2013.01); *C12Q 1/6869* (2013.01); *C40B 40/06* (2013.01); *C12Q 2563/185* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,661,450 A | 4/1987 | Kempe et al. | |
| 6,812,023 B1 | 11/2004 | Lamparski et al. | |
| 6,899,863 B1 | 5/2005 | Dhellin et al. | |
| 7,198,923 B1 | 4/2007 | Abrignani et al. | |
| 2006/0160090 A1 | 7/2006 | Macina et al. | |
| 2008/0286769 A1 * | 11/2008 | Stenman | C12Q 1/6851 435/6.1 |
| 2010/0196426 A1 | 8/2010 | Skog et al. | |
| 2011/0003704 A1 | 1/2011 | Skog et al. | |
| 2011/0053157 A1 | 3/2011 | Skog et al. | |
| 2011/0151460 A1 | 6/2011 | Klass et al. | |
| 2013/0130241 A1 | 5/2013 | Dehm | |
| 2013/0131194 A1 | 5/2013 | Skog et al. | |
| 2014/0235470 A1 | 8/2014 | Olivares et al. | |
| 2015/0051088 A1 | 2/2015 | Kim | |
| 2015/0233927 A1 | 8/2015 | Giannakakou et al. | |
| 2015/0329891 A1 * | 11/2015 | Tan | C12Q 1/6806 435/320.1 |
| 2015/0374721 A1 * | 12/2015 | Njar | A61P 13/08 514/176 |
| 2016/0024572 A1 * | 1/2016 | Shishkin | C12Q 1/6806 506/2 |
| 2016/0040229 A1 * | 2/2016 | Talasaz et al. | G16B 30/10 506/26 |
| 2017/0009274 A1 | 1/2017 | Abate et al. | |
| 2020/0024644 A1 | 1/2020 | Wang et al. | |
| 2021/0102256 A1 | 4/2021 | Jia et al. | |

FOREIGN PATENT DOCUMENTS

| | | | | |
|---|---|---|---|---|
| EP | 2774997 A1 * | 9/2014 | | C12Q 1/686 |
| WO | WO-2007131354 A1 * | 11/2007 | | B01J 19/0046 |
| WO | WO-2009100029 A1 | 8/2009 | | |
| WO | WO-2011009104 A1 | 1/2011 | | |
| WO | WO-2011031877 A1 | 3/2011 | | |
| WO | WO-2011031892 A1 | 3/2011 | | |
| WO | WO-2012129363 A2 * | 9/2012 | | C12N 15/1065 |

(Continued)

OTHER PUBLICATIONS

Attard, et al. Prostate cancer. Lancet. Jan. 2, 2016;387(10013):70-82. doi: 10.1016/S0140-6736(14)61947-4. Epub Jun. 11, 2015.
Chen, et al. Microfluidic isolation and transcriptome analysis of serum microvesicles. Lab Chip. Feb. 21, 2010;10(4):505-511. doi: 10.1039/b916199f. Epub Dec. 8, 2009.
Cheruvanky, et al. Rapid isolation of urinary exosomal biomarkers using a nanomembrane ultrafiltration concentrator. Am J Physiol Renal Physiol. May 2007;292(5):F1657-61. doi: 10.1152/ajprenal.00434.2006. Epub Jan. 16, 2007.
Fettke, et al. Combined Cell-free DNA and RNA Profiling of the Androgen Receptor: Clinical Utility of a Novel Multianalyte Liquid Biopsy Assay for Metastatic Prostate Cancer. Eur Urol. Aug. 2020;78(2):173-180. doi: 10.1016/j.eururo.2020.03.044. Epub May 30, 2020.
Gene Expression Omnibus. Accession No. GSE14996. Multisampled Lethal Metastatic Prostate Cancer Copy Number Analysis. Public on Apr. 12, 2009. 2 pages. Retrieved Feb. 25, 2021 at URL: https://www.ncbi.nlm.nih.gov/geo/query/acc.cgi?acc=GSE14996.

(Continued)

*Primary Examiner* — Bradley L. Sisson
(74) *Attorney, Agent, or Firm* — Wilson Sonsini Goodrich & Rosati

(57) ABSTRACT

Disclosed are systems and methods for detecting genetic alterations comprising androgen receptor gene splice variants (AR-Vs), mutations, indel, copy number changes, fusion and combination thereof, in a biofluid sample from the patient. The systems and methods are similarly applicable to the detection of gene alterations comprising gene splicing variants, mutations, indel, copy number changes, fusion and combination thereof of other genes of interest. The streamlined methods improve the consistency and simplicity of non-invasive detections of biomarkers.

20 Claims, 11 Drawing Sheets

(56) References Cited

FOREIGN PATENT DOCUMENTS

| WO | WO-2015031691 A1 | | 3/2015 | |
|---|---|---|---|---|
| WO | WO-2015179404 A1 | * | 11/2015 | ........... C12Q 1/6886 |
| WO | WO-2016138496 A1 | | 9/2016 | |
| WO | WO-2016141169 A1 | | 9/2016 | |
| WO | WO-2017027835 A1 | | 2/2017 | |
| WO | WO-2017181161 A1 | | 10/2017 | |
| WO | WO-2018057820 A1 | | 3/2018 | |
| WO | WO-2018183796 A1 | | 10/2018 | |

OTHER PUBLICATIONS

Gene Expression Omnibus. Accession No. GSE18333. Distinct genomic differences in prostate cancer between Western countries and China. Public on May 15, 2010. 2 pages. Retrieved Feb. 25, 2021 at URL: https://www.ncbi.nlm.nih.gov/geo/query/acc.cgi?acc=GSE18333.

Guo et al. A novel androgen receptor splice variant is up-regulated during prostate cancer progression and promotes androgen depletion-resistant growth. Cancer Res 69:2305-2313 (2009).

Hinrichs, et al. Comparison of next-generation sequencing and mutation-specific platforms in clinical practice. Am J Clin Pathol. Apr. 2015;143(4):573-578. doi: 10.1309/AJCP40XETVYAMJPY.

Hu et al. Ligand-Independent Androgen Receptor Variants Derived from Splicing Cryptic Exons Signify Hormone-Refractory Prostate Cancer. Cancer Res 69:16-22 (2009).

Imboden, et al. Simultaneous detection of DNA and RNA by differential polymerase chain reaction (DIFF-PCR). Genome Research. Aug. 1993;3(1):23-27. doi: 10.1101/gr.3.1.23.

International search report with written opinion dated Jul. 5, 2017 for PCT/US2017/027830.

International search report with written opinion dated Jul. 16, 2018 for PCT/US2018/025335.

International search report with written opinion dated Dec. 7, 2017 for PCT/US2017/052832.

Jia, et al. Emerging technologies in extracellular vesicle-based molecular diagnostics. Expert Rev Mol Diagn. Epub Feb. 27, 2014. pp. 1-15. doi: 10.1586/14737159.2014.893828.

Kohli, et al. Clinical and genomic insights into circulating tumor DNA-based alterations across the spectrum of metastatic hormone-sensitive and castrate-resistant prostate cancer. EBioMedicine. Apr. 2020;54:102728. doi: 10.1016/j.ebiom.2020.102728.

Miranda, et al. Nucleic acids within urinary exosomes/microvesicles are potential biomarkers for renal disease. Kidney Int. Jul. 2010;78(2):191-199. doi: 10.1038/ki.2010.106. Epub Apr. 28, 2010.

Mogi, et al. TP53 mutations in nonsmall cell lung cancer. J Biomed Biotechnol. 2011. vol. 2011, Article ID 583929. 9 pages, doi: 10.1155/2011/583929. Epub Jan. 18, 2011.

Nilsson, et al. Prostate cancer-derived urine exosomes: a novel approach to biomarkers for prostate cancer. Br J Cancer. May 19, 2009; 100(10): 1603-1607. Published online Apr. 28, 2009. doi: 10.1038/sj.bjc.6605058.

Poritz, et al. FilmArray, an automated nested multiplex PCR system for multi-pathogen detection: development and application to respiratory tract infection. PLoS One. 2011;6(10):e26047. doi: 10.1371/journal.pone.0026047. Epub Oct. 19, 2011.

Predicine, Inc. PrediSeq Pan Cancer Panel. Product Datasheet [online], Mar. 22, 2017. Retrieved on Nov. 16, 2017 from the Internet at URL: http://www.predicine.org/uploads/4/6/3/9/46396713/lung_panel_v5.pdf.

Raposo, et al. B lymphocytes secrete antigen-presenting vesicles. J Exp Med. Mar. 1, 1996;183(3):1161-1172. doi: 10.1084/jem.183.3.1161.

Ribeiro, et al. Early detection and personalized treatment in oral cancer: the impact of omics approaches. Mol Cytogenet. 2016; 9:85. Published online Nov. 23, 2016. doi: 10.1186/s13039-016-0293-1.

Shames, et al. A genome-wide screen for promoter methylation in lung cancer identifies novel methylation markers for multiple malignancies. PLoS Med. Dec. 2006;3(12):e486. doi: 10.1371/journal.pmed.0030486.

Skog, et al. Glioblastoma microvesicles transport RNA and proteins that promote tumour growth and provide diagnostic biomarkers. Nat Cell Biol. Dec. 2008;10(12):1470-1476. doi: 10.1038/ncb1800. Epub Nov. 16, 2008.

Tarailo-Graovac, et al. Using RepeatMasker to identify repetitive elements in genomic sequences. Curr Protoc Bioinformatics. Mar. 2009; Chapter 4:Unit 4.10. doi: 10.1002/0471250953.bi0410s25.

Taylor, et al. MicroRNA signatures of tumor-derived exosomes as diagnostic biomarkers of ovarian cancer. Gynecol Oncol. Jul. 2008;110(1):13-21. doi: 10.1016/j.ygyno.2008.04.033.

Walter, et al. DNA methylation profiling defines clinically relevant biological subsets of non-small cell lung cancer. Clin Cancer Res. Apr. 15, 2012;18(8):2360-2373. doi: 10.1158/1078-0432.CCR-11-2635-T. Epub Jan. 19, 2012.

* cited by examiner

SYSTEMS AND METHODS FOR DETECTING GENETIC ALTERATIONS

FIELD OF INVENTION

The invention relates generally to the field of precision medicine, specifically cancer prediction, diagnostics or prognostics, and, more specifically of Gene RADAR and PCR methods for predicting resistance to androgen receptor-targeted therapies in a prostate cancer patient by the detection of genetic alterations including RNA-based androgen receptor (AR) splicing variants (AR-Vs), including but not limited to, AR-V7, AR-V567es, AR-V9, together with additional genetic alterations including, but not limited to, DNA- and/or RNA-based mutation, indel, copy number variation, gene fusions from biofluid samples, e.g., plasma, serum, urine, and saliva etc.

BACKGROUND

Prostate cancer is the most commonly diagnosed cancer and the 3rd most common cause of cancer-related death in the United States. About 10%-20% of men with prostate cancer will advance to castration resistant prostate cancer (CRPC). Expression of AR-Vs has been shown to correlate with disease progression and shortened survival. Treatment of CRPC is supported by the efficacy of newer AR-directed therapies with: (i) androgen synthesis inhibitors; (ii) AR-signaling inhibitors. Understanding the mechanisms of response and resistance to AR-directed agents may help improve treatment outcome.

Some data suggests that genetic alterations in AR gene, including, RNA-based splicing variant such as AR-V7, and DNA-based mutations such as AR-T878A, AR-F876L, may drive resistance in CRPC. Expression of AR-Vs has been shown to correlate with disease progression and shortened survival and AR-V7 is most abundant in CRPC specimens. Considering that truncated AR-Vs with C-terminal loss (splice variants) lack a functional ligand binding domain (LBD) and are constitutively active, C-terminal AR-directed therapies may not be effective and novels agents are needed that target mutated ARs including AR-Vs.

Circulating tumor cells (CTCs) are emerging as a source of information in therapy-resistant prostate cancer patients. CTC can be obtained through non-invasive means, opening the door to serial assessments of the disease state and examine tumor cell response to therapy. Recent CTC studies suggested that detection of AR-V7 in CTCs from men with metastatic castration resistant prostate cancer (mCRPC) was associated with resistance to both enzalutamide and abiraterone, as evidenced by inferior PSA50 response rates, profession free survival (PFS) and overall survival (OS). These results suggest that the AR-V7 status may be used as a predictive (i.e. for treatment selection) or prognostic non-invasive biomarker in patients treated with AR-targeting agents.

However, one key limitation of using CTC in mCRPC prediction is the lack of detectable CTCs (less than 5 CTCs per 7.5 ml) in the majority of mCRPC patients, thus limiting the potential of CTC-based detection of RNA splicing variants such as AR-V7. Therefore, it is desirable to have a new method for CRPC prediction without the limitation of using CTCs.

BRIEF SUMMARY OF THE INVENTION

The present invention provides a method for detecting a genetic alteration from a biofluid comprises: a) obtaining nucleic acids from the biofluid and preparing two portions of sample wherein one portion comprises s single strand RNA (ssRNA) and the other portion comprises a double strand DNA(dsDNA), b) barcoding ss RNA and converting ssRNA to dsDNA wherein the dsDNA is a barcoded dsDNA, and c) mixing the barcoded dsDNA and the dsDNA portion for further genetic alteration analysis.

The present invention further provides that the bardcoded dsDNA is obtained by reverse transcribing ssRNA to dsDNA after ss RNA is ligated to one or more oligonucleotides. The genetic alterations to be detected comprising one or more gene splice variants (AR-Vs), mutations, indels, copy numbers changes, fusions and combination thereof.

The biofluid samples are selected from a group consisting of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascetic fluid, tumor cyst fluid, amniotic fluid, and a combination thereof.

The bardcoded DNA mixture is subsequently analysed by Next Generation Sequencing, Polymerase Chain Reaction, and/or array-based technologies.

The present invention further comprises he detection of presence and absence of a genetic alteration is indicative of a disease and the disease is one or more cancers, for example, a genetic alteration is from an androgen receptor gene mutation which predicts prostate cancer.

The present invention provides a method for predicting resistance to androgen receptor (AR) targeted therapy in a prostate cancer patient, comprising: assaying the presence or absence of CRPC-related genetic alterations in a biofluid from the patient; wherein the presence or absence of DNA- and/or RNA-based genetic alterations indicates the presence of resistance to AR targeted therapy in the prostate cancer patient.

The present invention further provides a system for detecting a genetic alteration from a biofluid comprises: a) obtaining nucleic acids from the biofluid and preparing two portions of sample wherein one portion comprises s single strand RNA (ssRNA) and the other portion comprises a double strand DNA(dsDNA), b) barcoding ss RNA and converting ssRNA to dsDNA wherein the dsDNA is a barcoded dsDNA, and c) mixing the barcoded dsDNA and the dsDNA portion for further genetic alteration analysis.

The system can be a closed system and an automated system.

The present invention further provides a platform for detecting multiple androgen receptor variants in a patient, comprising: (a) a kit of reagents for circulating nucleic acid extraction and oligonucleotides targeting one or more gene alterations; and (b) bioinformatics analysis solution to decipher DNA and RNA-derived information.

The present invention further provides a kit and device for the detection genetic alterations.

Disclosed are systems and methods for detecting genetic alterations in castration resistant prostate cancer patient. In one aspect, the disclosed method comprises assaying the presence or absence of one or more androgen receptor gene splice variants (AR-Vs) and additional genetic alterations such as mutation, indels, copy number variation, gene fusions etc. in a biofluid sample from the patient.

In some embodiments, the biofluid sample is a sample of blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascetic fluid, tumor cyst fluid, amniotic fluid, or a combination thereof.

In some embodiments, the step of assaying comprises extracting RNA from the biofluid sample and subsequently reverse transcribing the extracted RNA into a complementary DNA.

In other embodiments, the step of assaying comprised extracting both DNA and RNA from the biofluid sample simultaneously and then reverse transcribing the extracted RNA to a complementary DNA.

In some embodiments, the resultant complementary DNA is subsequently measured by Next Generation Sequencing, Polymerase Chain Reaction including qPCR and digital PCR, array-based technologies, and other related technologies.

In another aspect, the method is for predicting resistance to androgen receptor (AR) targeted therapy in a prostate cancer patient. In some embodiments, the method comprises assaying the presence or absence of CRPC-related genetic alterations in a biofluid sample from the patient; wherein the presence or absence of DNA- and/or RNA-based genetic alterations indicates the presence of resistance to AR targeted therapy in the prostate cancer patient.

Also disclosed is a platform for detecting an androgen receptor variant in a patient, comprising: (a) a kit comprising reagents for circulating nucleic acid extraction, including DNA, RNA, small RNA including microRNA, and other biological materials and oligos targeting the androgen receptor genetic alterations; and (b) bioinformatics analysis solution to decipher DNA and RNA-derived information.

In other embodiments, the bioinformatics analysis can separate the DNA and RNA reads based on the RNA-specific barcodes and integrate the RNA and DNA information to detect genetic alteration comprising gene slicing variations, SNV, Indel, CNV, with increased sensitivity and specificity.

DETAILED DESCRIPTION OF THE INVENTION

Figure 1:
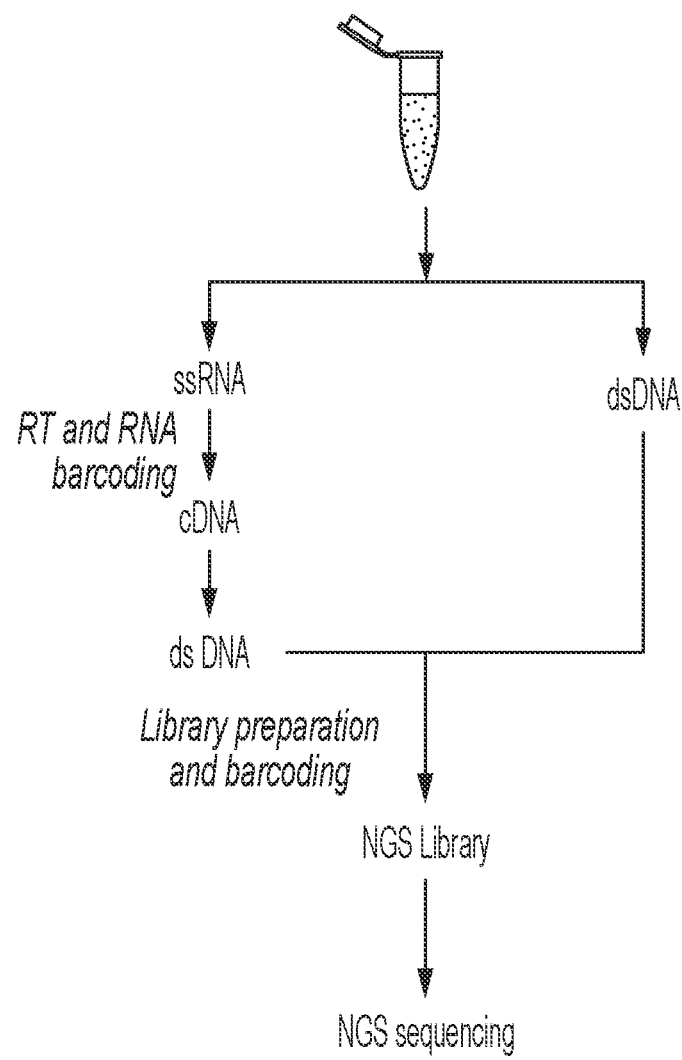
FIG. 1 shows a Gene RADAR (RNA and DNA single molecular digital Reading) assay flowchart depicting the steps from biofluid to wet lab testing and data analysis of RNA- and DNA-derived genetic alterations.

The present invention provides a method for detecting a genetic alteration from a biofluid. The present invention provides an extraction method for obtaining nucleic acids from the biofluid samples.

In one embodiment, the samples include but are not limited to blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, and a combination thereof.

The present invention further provides that dividing of samples into two portions, one portion is double stranded DNA and the other portion is single stranded RNA. The method for preparation is known to one of the skills in the art.

The present invention provides a method for barcoding an oligonucleotide tag on the RNA sample by reserve transcribing it to cDNA and dsDNA. In one embodiment, the oligo nucleotide consists of 5, 10, 12, 14, 15, 20 nucleic acid bases. In another embodiment, the oligo nucleotide can be designed for fitting the identification in further analysis. In another embodiment, the barcoding process is by ligation an oligonucleotide to ssRNA.

In another embodiment, the tagged dsDNA is mixed with the other portion of the dsDNA extract to use for further genetic analysis including but not limited to sequencing assay such as Next Generation Sequencing, Polymerase Chain Reaction, array-based technologies and/or cytogenetics assay.

The genetic alterations include but are not limited to gene splice variants (AR-Vs), mutations, indels, copy number changes, fusions and combination thereof. The method of detecting the alterations is used to detect the changes of above.

The present invention further comprises he detection of presence and absence of a genetic alteration is indicative of a disease and the disease is one or more cancers. One embodiment, genetic alteration detection is to detect an androgen receptor gene variation.

In one embodiment, the present invention provides a method for predicting resistance to androgen receptor (AR) targeted therapy in a prostate cancer patient.

The embodiment further comprises assaying the presence or absence of CRPC-related genetic alterations in a biofluid from the patient; wherein the presence or absence of DNA- and/or RNA-based genetic alterations indicates the presence of resistance to AR targeted therapy in the prostate cancer patient.

The present invention further provides a system for detecting a genetic alteration from a biofluid comprises: a) obtaining nucleic acids from the biofluid and preparing two portions of sample wherein one portion comprises s single strand RNA (ssRNA) and the other portion comprises a double strand DNA(dsDNA), b) barcoding ss RNA and converting ssRNA to dsDNA wherein the dsDNA is a barcoded dsDNA, and c) mixing the barcoded dsDNA and the dsDNA portion for further genetic alteration analysis.

The system can be an opened or closed system. And both systems can be automated system. The system can be in a device setting.

The present invention further provides a platform for detecting multiple androgen receptor variants in a patient, comprising: (a) a kit of reagents for circulating nucleic acid extraction and oligos targeting one or more gene alterations; and (b) bioinformatics analysis solution to decipher DNA and RNA-derived information.

The present invention further provides a kit the detection genetic alterations.

In further embodiment, the present invention is based, in part, on a novel method for identifying biomarker that enables prospective prediction of resistance to AR targeted therapies in a patient afflicted with mCRPC. The novel method employs a CTC-independent approach to isolate RNA and DNA from a biofluid sample. There are abundant cell-free RNA (cfRNA) and extracellular vesicles in all people including patients and the abundance of cfRNA and extracellular vesicles is independent of the number of CTCs. Hence, the novel method enables the detection of genetic alterations in more patients than CTC-based methods.

In one aspect, the present disclosure allows the detection of RNA splice variant of many genes, in addition to Androgen Receptor as an example used here, from biofluids in specimens of various sources. In some embodiments, the disclosed novel method streamlines the extraction of circulating RNA from biofluids, reverse transcription of targeted region of interest and NGS library preparation and sequencing. In contrast to existing methods known in the art, this streamlined process enables the non-invasive detection of RNA splice variant of interest by using biofluid samples in a quick, simplified, and consistent manner.

In another aspect, the disclosed method also allows for the reverse transcribed RNA (cDNA) to be included in the mainstream cfDNA library preparation and target enrichment protocol thereby allowing consolidated result of both DNA and RNA from a single biofluid sample. For example, cfDNA and cfRNA are extracted simultaneously, and then the extracted sample are used for reverse transcription and further used for the library processing and sequencing. In the process, there is no need to separate cfDNA from the cfRNA in the biofluid nucleic acid extraction. In some instances, to distinguish the DNA- and RNA-derived signals, the extracted RNA is barcoded according to methods known in the art and reverse transcribed in a single step before the steps of library preparation and sequencing.

In some embodiments, the present disclosure provides a method for detecting castration resistant prostate cancer in a patient comprising assaying the presence or absence of one or more types of genetic alterations at both RNA and DNA levels, such as androgen receptor gene RNA splice variants (AR-Vs) and RNA/DNA-based mutation detection in a biofluid sample from the patient; wherein the presence of such genetic alterations indicates the presence of the castration resistant prostate cancer in the patient. In some embodiments, the castration resistance is de novo resistance. In other embodiments, the castration resistance preexists. In some particular embodiments, the prostate cancer is metastatic castration resistant prostate cancer (mCRPC).

In some embodiments, RNA alone is extracted from circulating RNA inside and outside of extracellular vesicles in a biofluid sample for further assay. In other embodiments, RNA is extracted together with DNAs from circulating nucleic acid and nucleic acid-containing extracellular vesicles in a biofluid sample. In the latter embodiments, no extra step of RNA purification is needed and therefore the process is simplified.

In some embodiments, the sources of nucleic acids are extracellular vesicles (EVs), including exosomes and microvesicles, which have been shown to carry a variety of biomacromolecules including mRNA, microRNA and other non-coding RNAs and considered to be a minimally invasive novel source of materials for molecular diagnostics. See Jia et al., "Emerging technologies in extracellular vesicle-based molecular diagnostics", Expert Rev. Mol. Diagn. 1-15 (2014). EVs are membranous, cell-derived, mixed populations of vesicles, ranging from approximately 40-5000 nm in diameter, which are released by a variety of cells into the intercellular microenvironment and various extracellular biofluids. Methods for procuring a microvesicle fraction from a biofluid sample are described in scientific publications and patent applications (Chen et al., 2010; Miranda et al., 2010; Skog et al., 2008). See also WO 2009/100029, WO 2011009104, WO 2011031892, and WO 2011031877. For example, methods of microvesicle procurement by differential centrifugation are described in a paper by Raposo et al. (Raposo et al., 1996), a paper by Skog et al. (Skog et al., 2008) and a paper by Nilsson et. al. (Nilsson et al., 2009). Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel-Taylor (Taylor and Gercel-Taylor, 2008). A method of nanomembrane ultrafiltration concentration is described in a paper by Cheruvanky et al. (Cheruvanky et al., 2007). Further, microvesicles can be identified and isolated from a subject's bodily fluid by a microchip technology that uses a microfluidic platform to separate tumor-derived microvesicles (Chen et al., 2010).

Methods for nucleic acid extraction are generally based on procedures well-known in the art plus proprietary procedures developed in-house. Persons of skill will select a particular extraction procedure as appropriate for the particular biological sample. Examples of extraction procedures are provided in patent publications WO/2009/100029, US 20100196426, US 20110003704, US 20110053157, WO 2011009104, WO 2011031892, US20130131194 and US20110151460. Each of the foregoing references is incorporated by reference herein for its teaching of these methods.

Many biofluids contain circulating nucleic acids and/or nucleic acid-containing EVs. Examples of these biofluids include blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, or a combination thereof.

In some embodiments, the biofluid sample is obtained from a subject who has been diagnosed with prostate cancer based on tissue or liquid biopsy and/or surgery or clinical grounds. In some embodiments, the biofluid sample is obtained from a subject showing a clinical manifestation of prostate cancer advancing to CRPC, including without limitation, rising PSA levels prior to diagnosis, after initial surgery or radiation, or despite hormone therapy. In some embodiments, the biofluid sample is obtained from a subject who has been on hormone therapy or who has had a bilateral orchiectomy and whose testosterone levels have dropped to less than 50 ng/dl, and who shows evidence of disease progression in the form of rising PSA levels or bone or soft tissue metastases. In some instances, the biofluid sample is obtained from a subject who has been undergoing primary hormone therapies, which are the LHRH agonists, for example, leuprolide (Lupron) or goserelin (Zoladex). In other embodiments, the biofluid sample is obtained from a healthy subject or a subject deemed to be at high risk for prostate cancer and/or metastasis of existing prostate cancer based on known clinically established criteria including, for example, age, race, family and history.

In some embodiments, the AR splicing variant detected in the present disclosure has a functional DNA binding domain, but not a functional ligand binding domain. In some instances, the AR splicing variant includes the entire or at least a functional portion of exon 1 encoding the N-terminal domain and the entire or at least a functional portion of exons 2 and 3 encoding the DNA binding domain, but does not include at least a functional portion of exon 4 encoding the short hinge region or at least a functional portion of exons 4-8 encoding the ligand binding domain. In other instances, the AR splicing variant that substantially consists of exons 1-3 may also include a non-functional portion of the nucleic acid sequence from a genomic region or exons 4-8. It is contemplated that the splicing process may give rise to such AR splicing variants that retain DNA binding function but not ligand binding function, indicative of a castrate-resistant prostate cancer.

In some embodiments, the androgen receptor gene splice variant is a truncated AR with C-terminal loss and therefore lacking LBD. In some instance, the LBD-lacking truncated AR variant is AR-V7, AR-V9, ARv567es or other known or novel splicing variants. In other instance, the AR genetic alteration is AR-T878A or other related mutation, copy number gain, RNA over expression, among others.

In some embodiments, the present disclosure provides a method of detecting genetic alterations related to resistance to androgen receptor (AR) targeted therapy in a prostate cancer patient comprising assaying the presence or absence of one or more androgen receptor genetic alterations in a biofluid sample from the patient; wherein the presence of the one or more AR-Vs indicates the presence of resistance to AR-targeted therapy in the prostate cancer patient. In some embodiments, the castration resistance is de novo resistance. In other embodiments, the castration resistance preexists. In some particular embodiments, the prostate cancer is metastatic castration-resistant prostate cancer (mCRPC).

In some embodiments, the prediction of resistance to AR-targeted therapy informs a subsequent treatment decision. Androgens in the form of testosterone or the more potent dihydrotestosterone (DHT) have been well-defined drivers of progression of prostate cancer and differentiation of the prostate gland. As such, the backbone of treatment for advanced prostate cancers was established decades ago when castration in the form of surgical orchiectomy achieved significant prostate tumor regression. Since then, substitution to chemical castration has been employed mostly due to patient preference. Androgen Deprivation Therapy (ADT) has therefore become the standard systemic treatment for locally advanced or metastatic prostate cancer. While ADT is almost always effective in most patients, disease progression to castration resistance inevitably occurs. It is now recognized that the androgen receptor (AR) remains overexpressed despite seemingly castrate levels of testosterone since alternative receptors may activate the AR or other target genes may help perpetuate the castrate-resistant phenotype, hence the term "castration-resistance" has become widely adopted in the literature.

The androgen receptor axis is a validated target for the treatment of castration-resistant prostate cancer. Several perturbations in this pathway are postulated to lead to androgen-independent growth, including androgen receptor mutation and amplification as well as the autocrine production of testosterone. Two drugs targeting this pathway in castration-resistant prostate cancer—abiraterone acetate (Zytiga®) and enzalutamide (Xtandi®)—are approved for use in prostate cancer patients. Mechanistically, abiraterone exerts antitumor activity by inhibition of the 17,20-lyase pathway, crucial to testosterone synthesis. Enzalutamide binds to the androgen receptor and prevents its translocation into the nucleus. Abiraterone is also approved for patients in the prechemotherapy setting based on results of recent clinical trials.

With new systemic therapies available, the optimal treatment sequence of these drugs in mCRPC becomes increasingly important. Chemotherapy is often indicated in the treatment of castration-resistant prostate cancer, and taxane-based agents, such as docetaxel, are often the first choice. Abiraterone (Zytiga), an anti-androgen drug, was initially only approved for the treatment of castration-resistant prostate cancer after chemotherapy. However, due to successful treatment results, many physicians currently prescribe abiraterone early during the course of treatment. Combining abiraterone with enzalutamide appears safe, and the efficacy of this combination over enzalutamide alone is being presently being evaluated to detect a survival advantage for the combination approach as upfront treatment as compared to the expected standard sequential use of these agents. Recent studies have suggested that since taxane-based chemotherapy and abiraterone are effective partially due to similar mechanisms, prior abiraterone treatment may contribute to taxane resistance and decreased chemotherapy effectiveness, suggesting clinical cross-resistance. The present methods enable optimal sequencing of care between hormone agents (abiraterone and enzalutamide) and cytotoxic chemotherapy (docetaxel and cabazitaxel).

In one embodiment, barcode or barcoding with random oligonucleotide sequences such as 5, 10, 12, 14, 15 nucleotides to uniquely tag individual target DNA molecules can be used. Such application increases the accuracy and reduce sequencing. For example, it can be used for PCR or NGS analysis to identify individual molecules (DNA or RNA fragments) in samples.

It must be noted that, as used in this specification and the appended claims, the singular forms "a", "an" and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

The term "patient," as used herein preferably refers to a human, but also encompasses other mammals. It is noted that, as used herein, the terms "organism," "individual," "subject," or "patient" are used as synonyms and interchangeably.

The term "genetic alteration" comprise gene splice variants, SNV, InDel, CNV, fusion and combination thereof.

The term "barcoding" or "barcode" means using one or more oligonucleotides as tags/markers to incorporate into a dsDNA. Such tagged dsDNA is used for future analysis.

The term "androgen receptor targeted therapy" or "AR-targeted therapy" in the context of the methods described herein encompasses any therapy that directly or indirectly inhibits the AR signaling pathway, including, for example, through inactivation of androgen production, inactivation of androgen binding to the AR or inactivation of the AR directly. Any therapy that disrupts the AR signaling axis and inhibits the signaling pathway is therefore included in the term AR-targeted therapy. An example of direct inhibition, enzalutamide, also known as MDV3100, is one of the most frequently studied AR antagonists. Enzalutamide targets several steps in the AR-signaling pathway. Due to its increased binding affinity for the AR, it is able to block androgens from binding to the receptor, preventing nuclear translocation of the AR, DNA binding, and co-activator recruitment of the ligand-receptor complex. One of the more notable characteristics of enzalutamide is that it is able to bind and inhibit not only wild type but also mutant AR, which means point mutations of the AR that commonly occur after the progression of PCa which causes castration resistance. Another emerging agent in the treatment of CRPC is abiraterone acetate. While enzalutamide targets the AR directly, abiraterone acts by indirectly inhibiting the AR signaling pathway. CYP17, an enzyme of the cytochrome P450 family, is inhibited by abiraterone. This inhibition is significant because CYP17 plays a critical role in testosterone synthesis. Accordingly, inhibition of causes inhibition of testosterone synthesis, limiting the amount of androgens circulating in the body, thus also limiting the action of the AR. While castration is able to decrease testosterone and DHT synthesis, it does not remove all possible sources of androgens within the body, such as intratumoral or adrenal androgens. As will be understood by those skilled in the art, any mechanism of androgen inhibition is a potential avenue for AR-targeted therapy.

As used herein, the term "resistance" in the context of AR-targeted therapy or chemotherapy, including taxanes, means that the subject does not show a response to the therapy based on an underlying ability of tumor cells to escape the effect of the therapeutic agent. Resistance includes de novo resistance and acquired resistance. Cancer patients that exhibit de novo resistance do not respond to chemotherapy from the start. However, in acquired resistance, the cancer cells initially respond to a chemotherapeutic drug but eventually acquire resistance to it. The cells might also show cross-resistance to other structurally and mechanistically unrelated drugs—a phenomenon commonly known as multidrug resistance (MDR). Owing to the acquisition of MDR, treatment regimens that combine multiple agents with different targets are no longer effective.

EXAMPLES

Example 1: Detection of spiked in ARVs Oligos in cfDNA Extracted from a Biofluid sample.

The example describes the detailed steps of assaying the presence or absence of one or more androgen receptor gene splice variants (AR-Vs) in a biofluid sample with spiked in AR-Vs and AR-FL (WT) oligos in the cfDNA extracted from the biofluid sample.

Figure 2:
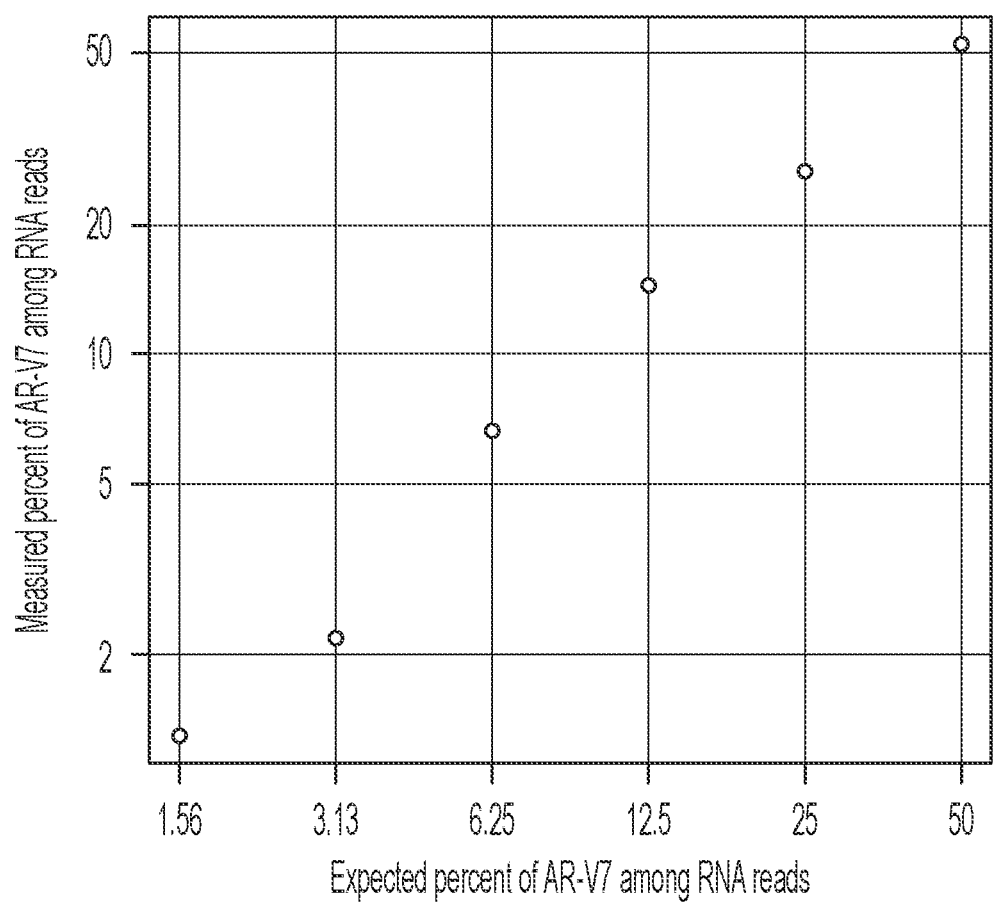
FIG. 2 shows a plot depicting the measured vs. expected percent of AR-V7 reads among all RNA reads. The titration experiment was performed in 6 levels of AR-V7 percentage: 1.56, 3.13, 6.25, 12.5, 25, and 50.

In this example, we used the Gene RADAR (RNA and DNA single molecular digital Reading) workflow, as shown in FIG. 1, to process about 5 ml plasma of healthy donor. We used optimized nucleic acid extraction procedure to extract RNA and DNA from plasma. Then cfDNA was size selected using Agencourt AMPure XP beads (Beckman Coulter) and subsequently quantified using Qubit 3.0 fluorometer. To mimic the condition that cDNAs, reverse transcription of targeted AR region, is mixed with cfDNA samples, AR-FL DNA fragment of 139 bp and AR-V7 DNA fragment of 125 bp were synthesized and pre-annealed, and then a mixer of AR-FL DNA fragment and AR-V7 DNA fragment equivalent to the copy number of cfDNAs were spiked into cfDNA samples. We performed a titration experiment of AR-V7 vs AR-FL spike into plasma. The titration experiment was performed in 6 levels of AR-V7 percent: 1.56, 3.13, 6.25, 12.5, 25, and 50.

cfDNA fragments were subsequently converted to digital sequence libraries according to the kit manufacturer's instructions with modification. Briefly, DNA was processed to end repaired, 5'-phosphorylated, and 3'-dA-tailed dsDNA fragments. Then DNA fragments were ligated to dsDNA adapters with 3'-dTMP overhangs. The libraries were amplified and then subsequently enriched for target genes using biotinylated custom baits of DNA probes and IDT xGen lockdown reagents. Enriched libraries were sequenced on NextSeq 500 (Illumina). As shown in FIG. 2, the measured percentage of AR-V7 reads is highly correlated with the expected percentage of AR-V7 reads.

Example 2: Detection of reverse transcribed AR-Vs in cfDNA and cfRNA extracted from a biofluid sample.

This example partly illustrates one embodiment of the disclosed method of detecting AR-V7 and AR-FL in castration-resistant prostate cancer patients.

Similar to Example 1, circulating nucleic acid is extracted from blood plasma samples using optimized nucleic acid extraction procedure. RNA in the above extraction is then reverse transcribed into cDNA.

In order to quantify the individual RNA molecules, we used two-layer RNA molecular barcoding scheme, as shown in FIG. 1. The first layer RNA molecular barcoding scheme includes adding RNA specific tags plus random molecular barcodes. After cDNA is converted as dsDNA (double-stranded DNA), it was the same as regular ds cfDNA. We then added the DNA level barcodes by ligation of adaptors.

For reverse transcription step, cDNA Synthesis Mix is prepared by adding sequentially 10× RT buffer, MgCl2, DTT, RNaseOUT, and SuperScript® III Reverse Transcriptase. The reverse transcription reaction was performed on thermocycler, then heat inactivated. Then RNA was removed. The cDNA synthesis reaction can be stored at −30° C. to −10° C.

To make the second strand from the cDNA, the following reagents are added to a 0.2-mL tube with 1st strand cDNA from above, DNA polymerase and AR specific primers (contain molecular barcode information). The second strand synthesis reaction is performed as follows: 37° C. for 60 min. The reaction is then cleaned up using a 2× AMPure XP beads according to the manufacturer's instructions. Quantification of DNA sample is performed using Qubit dsDNA High Sensitivity Assay kit and the DNA size distribution is analyzed using Agilent High Sensitivity DNA chips.

cfDNA fragments were subsequently used in PCR test or converted to NGS digital sequence libraries according to the commercial kit manufacturer's instructions with modification. Briefly, DNA was processed to end repaired, 5'-phosphorylated, and 3'-dA-tailed dsDNA fragments. Then DNA fragments were ligated to dsDNA adapters with 3'-dTMP overhangs. The adapters contain sample/molecular barcode information. The libraries were amplified, quantified, and then pooled together. The pooled libraries then subsequently enriched for target genes using biotinylated custom baits of DNA probes and IDT xGen lockdown reagents (IDT) according to the manufacturer's instructions with modification. Quantification of enriched libraries was performed using Qubit dsDNA High Sensitivity Assay kit and the DNA size distribution was analyzed using Agilent High Sensitivity DNA chips. Certain number of enriched libraries were denatured, diluted and loaded on NextSeq 500 (Illumina) for sequencing.

Figure 3:
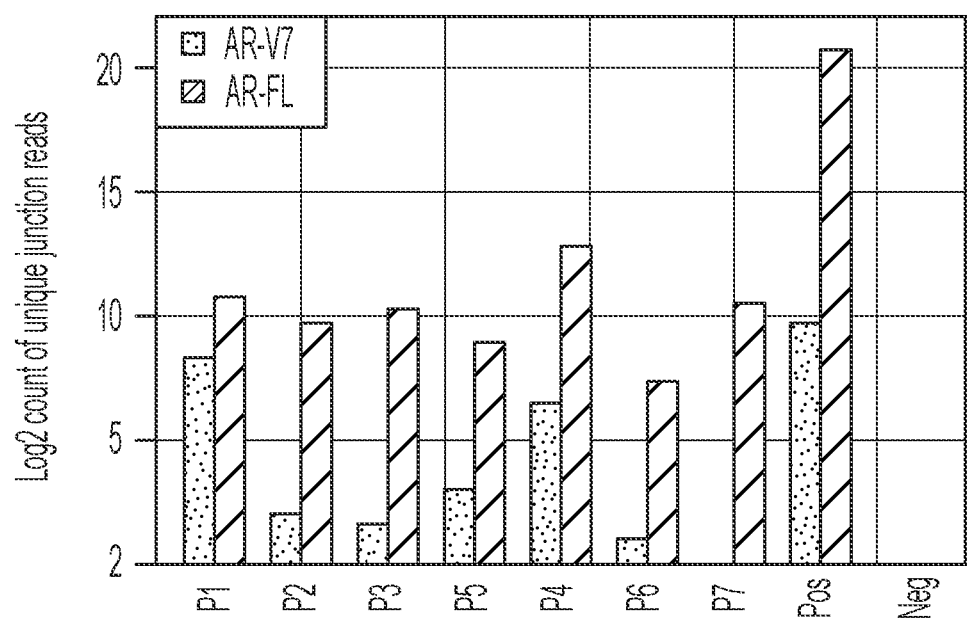
FIG. 3 shows the number of AR-V7 and AR-FL junction reads detected from clinical plasma samples by NGS. V-cap cell line was used as positive control.

FIG. 3 shows the analysis result, the AR-V7 and AR-FL specific junction read count. The result shows that AR-V7 junction reads were detected in 6 out of 7 samples. And no AR-V7 junction reads were detected in an AR-V7 negative control sample, and high level of AR-V7 junction reads was detected in the AR-V7 positive control sample (Vcap cell line).

Example 3: Detection of reverse transcribed novel AR-Vs in circulating nucleic acid extracted from a biofluid sample.

Similar to Example 1, circulating nucleic acid was extracted from blood plasma samples using optimized nucleic acid extraction procedure.

RNA in the above extraction is then reverse transcribed into cDNA. Specifically, in a 0.2 mL PCR tube with total nucleic acid extraction, primer, dNTP mix are mixed. The following cDNA Synthesis Mix was prepared by adding sequentially 10× RT buffer, MgCl2, DTT, RNaseOUT, and SuperScript® III Reverse Transcriptase. The reverse transcription reaction was performed on thermocycler, then heat inactivated. Then RNA was removed. The cDNA synthesis reaction can be stored at −30° C. to −10° C.

Second strand cDNA synthesis, and following library preparation, Enrichment, Sequencing on illumine NextSeq 500 procedure were same as Example 2.

Figure 4:
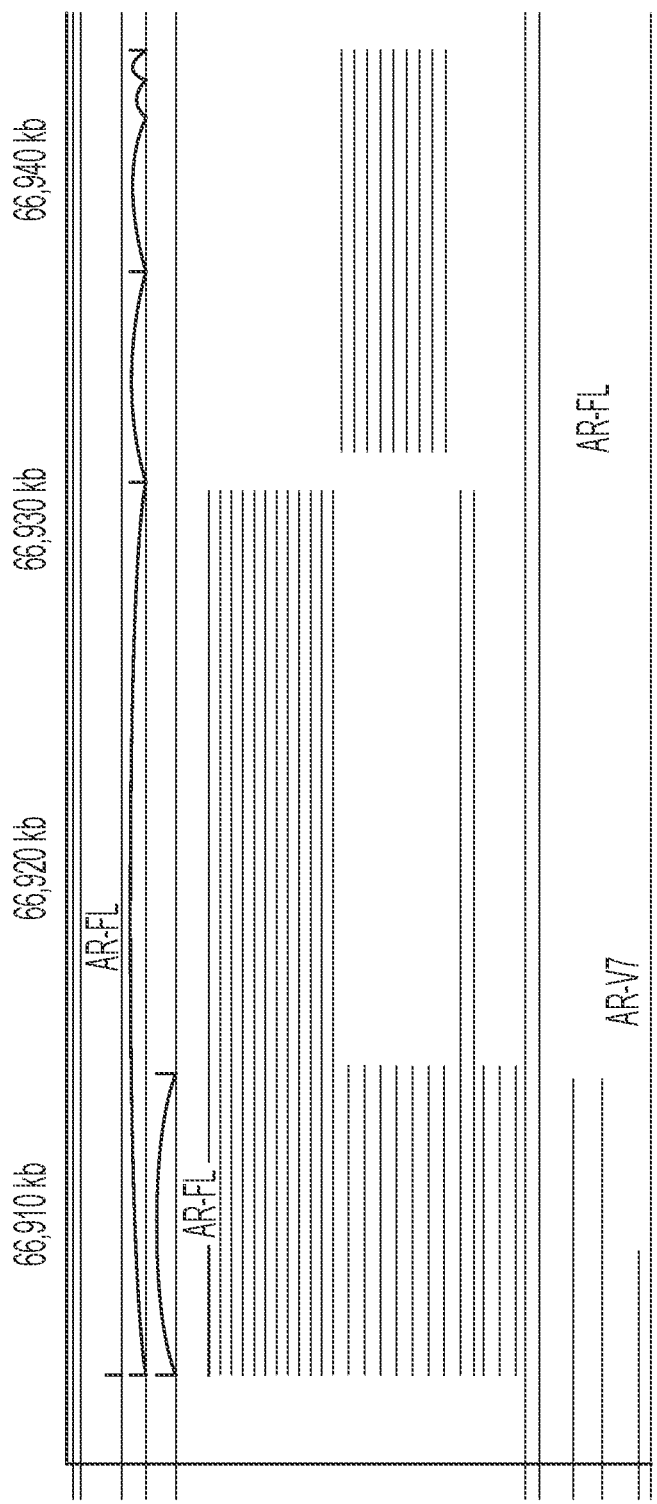
FIG. 4 shows an IGV (Integrative Genomics Viewer) screen shot describing the multiple AR splicing variants detected from one clinical plasma sample. The red arches represent the junction reads specific to the particular AR splicing variants.

FIG. 4 shows one example of detecting multiple AR splicing variants (AR-V1/V2, AR-V7, AR-V9 and AR-FL) from one clinical plasma sample. In FIG. 4, the read arches represented the junction reads across two exons.

Example 4: Detection of reverse transcribed fusion genes or other gene splicing isoforms in circulating nucleic acid extracted from a biofluid sample.

This example partly illustrates one embodiment of the disclosed method of detecting gene fusion or other gene splicing isoforms in prostate cancer patient biofluid samples.

Similar to Example 1, circulating nucleic acid was extracted from blood plasma samples using optimized nucleic acid extraction procedure.

RNA in the above extraction was then reverse transcribed into cDNA. Specifically, in a 0.2 mL PCR tube with total nucleic acid extraction random hexamer, all Predicine-designed fusion gene specific primers with a molecular barcode, dNTP mix are mixed. The following cDNA Synthesis Mix was prepared by adding sequentially 10× RT buffer, MgCl2, DTT, RNaseOUT, and SuperScript® III Reverse Transcriptase. The reverse transcription reaction was performed on thermocycler, then was heat inactivated. Then RNA was removed. The cDNA synthesis reaction can be stored at −30° C. to −10° C.

To make the second strand from the cDNA, the following reagents were added to a 0.2-mL tube with 1st Strand cDNA from above, DNA polymerase and Predicine-designed splicing/fusion gene specific primers (contain molecular barcode information). The second strand synthesis reaction was performed as follows: 37° C. for 60 min. The reaction was then cleaned up using a 2× AMPure XP beads according to the manufacturer's instructions. Quantification of DNA sample is performed using Qubit dsDNA High Sensitivity Assay kit and the DNA size distribution was analyzed using Agilent High Sensitivity DNA chips.

The following library preparation, Enrichment, Sequencing on Illumina sequencing platform were same as Example 2.

Figure 5A:
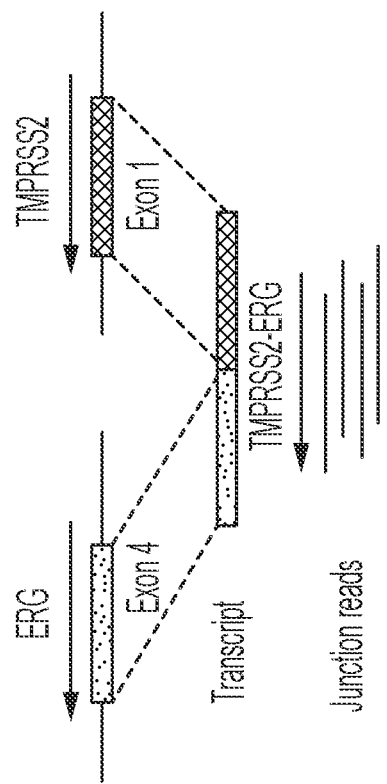
FIGS. 5A-5B show an example of TMPRSS2-ERG fusion detected in a prostate cancer patient plasma.
Figure 5B:
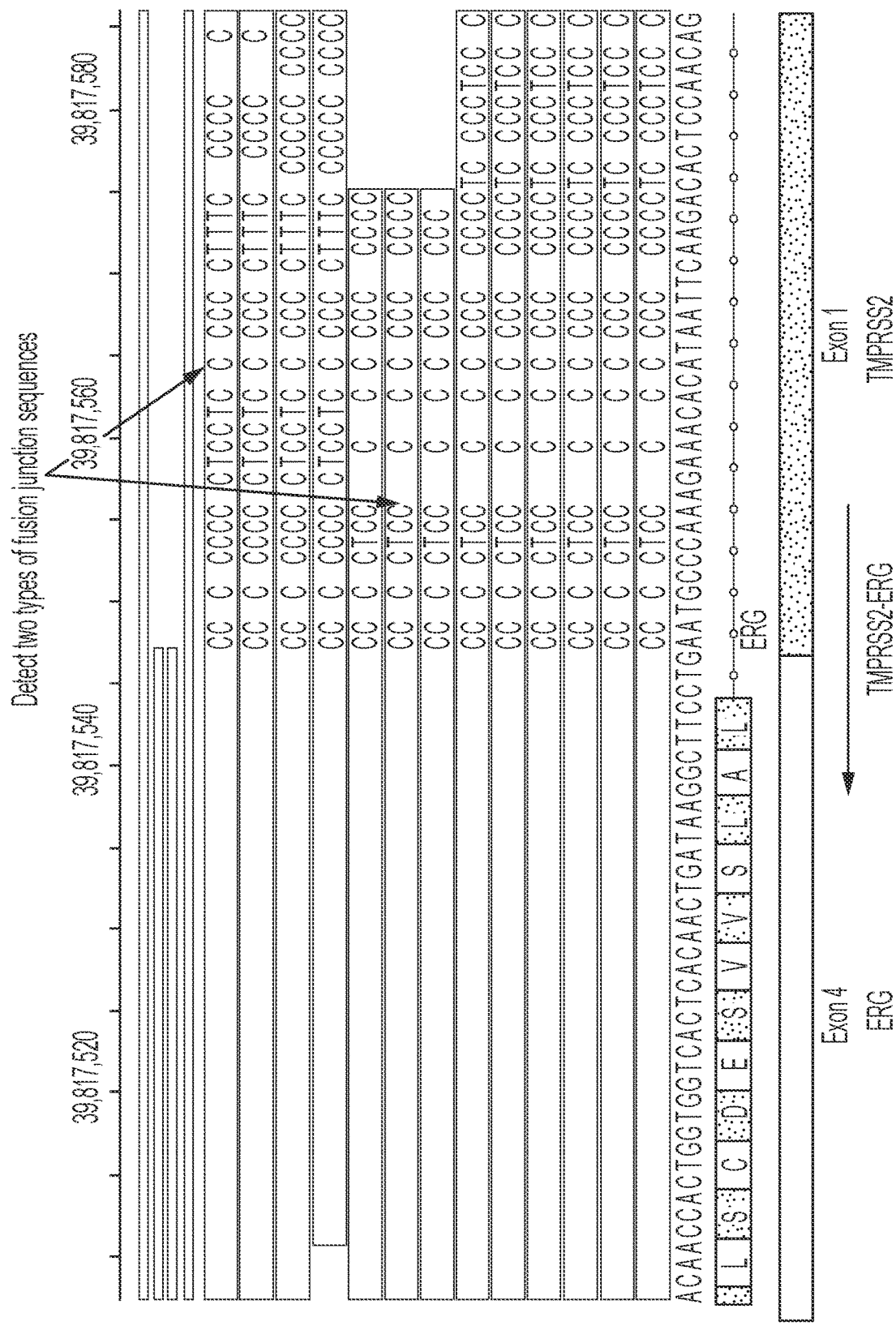

FIGS. 5A-5B show an example of TMPRSS2-ERG gene fusion was identified in a prostate cancer patient plasma. The left side of FIGS. 5A-5B show the gene model of the TMPRSS2-ERG fusion. The right side of FIGS. 5A-5B show the IGV screen shot of sequencing data from a patient plasma sample. The plot shows two types of fusion junction reads were identified.

Example 5: Detection of DNA copy number gains in the circulating nucleic acid extracted from a biofluid sample.

This example partly illustrates one embodiment of the disclosed method of detecting DNA copy number gains while measuring other RNA level variants at the same time from the patient biofluid sample.

Figure 6:
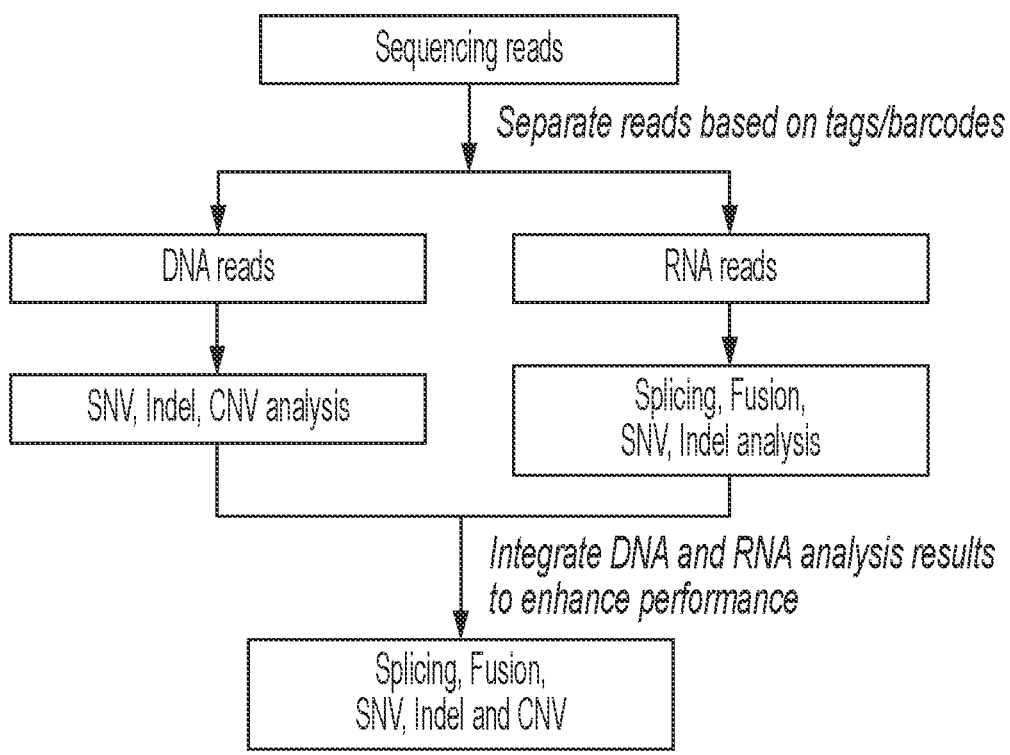
FIG. 6 shows the Gene RADAR Bioinformatics analysis workflow.

DNA copy number change is one of the important genomic abnormalities causing cancers. It is important to detect DNA copy number changes while detecting other RNA level variations in cancer patients. We used the Gene RADAR (RNA and DNA single molecular digital Reading) bioinformatics analysis workflow, as shown in FIG. 6, to analyze both DNA and RNA reads. The sequencing reads were first separated as RNA reads (with RNA specific tags/barcodes) and DNA reads (without RNA specific tags/barcodes). For DNA reads, we aligned the reads to human reference genome, and then calculate the consensus sequences based on molecular barcodes and alignment start and end location of the fragments using in-house developed algorithm. SNV, Indel variant calls, and CNV analysis were performed based on the bam file of aligned consensus sequences using in-house developed algorithms. For RNA reads, we first aligned the reads to human reference genome and transcriptome, calculated the consensus sequences based on molecular barcodes and alignment start and end location of the fragments using in-house developed algorithm. We counted the junction reads for splicing junctions of interest based on aligned consensus sequences. We detected SNV and Indels from RNA data. Finally, we integrated the DNA and RNA analysis results and received comprehensive variant analysis results.

Figure 7:
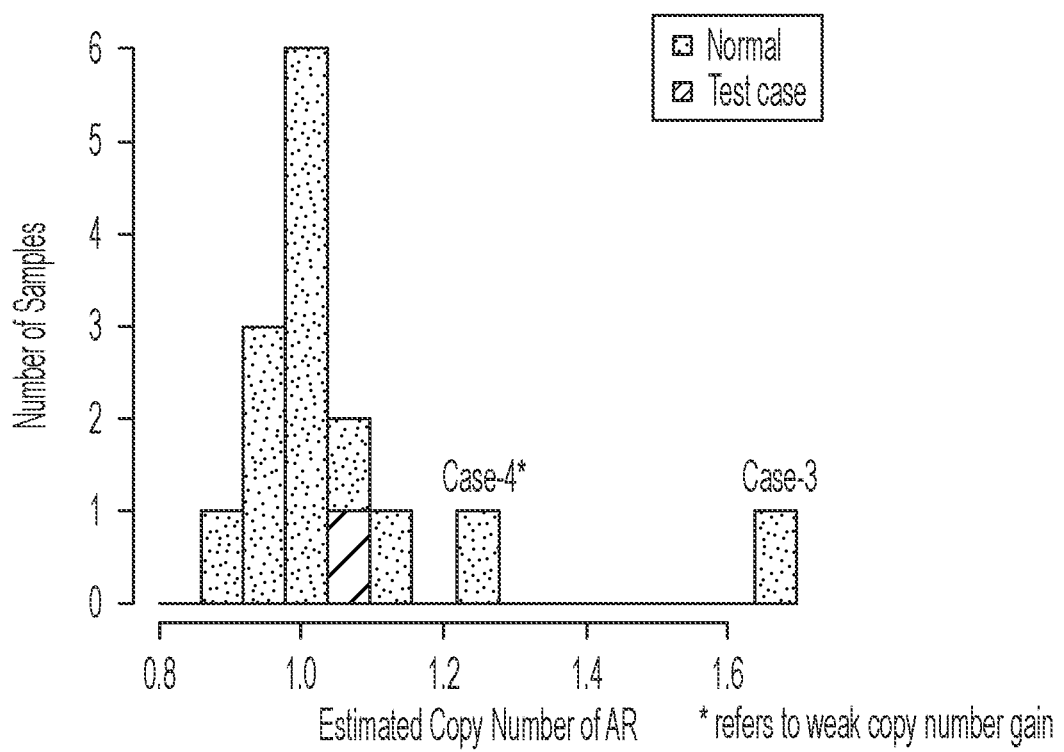
FIG. 7 shows an example of AR copy number gains detected in patient plasma samples.

FIG. 7 shows an example of detecting copy number changes following the analysis workflow shown in FIG. 6. FIG. 7 shows Case-3 has significant AR copy number gain while Case-4 has less significant AR copy number gains, and other two patients had their calculated AR copy numbers close to the normal control samples (shown in grey color).

Figure 8:
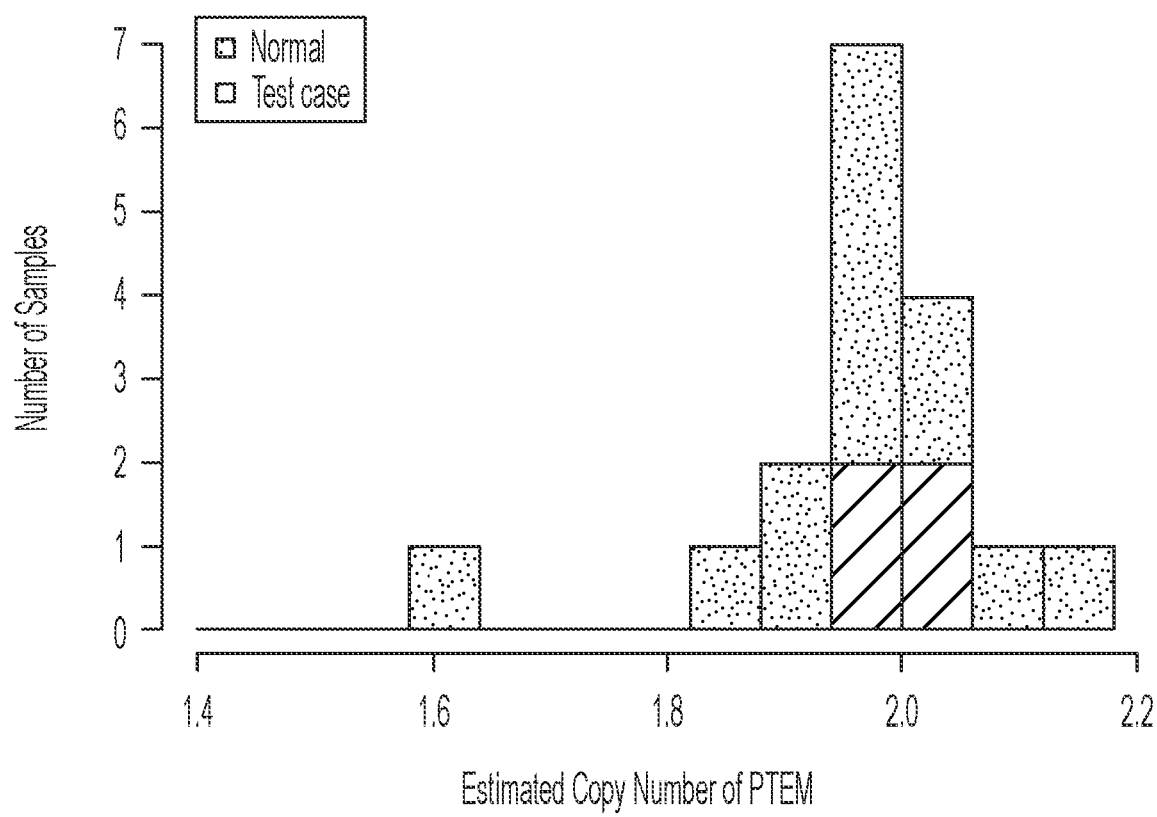
FIG. 8 shows an example of PTEN deletion detected in patient plasma samples.

Example 6: FIG. 8 shows an example of PTEN deletion detected in plasma samples of CRPC patient.

Figure 9:
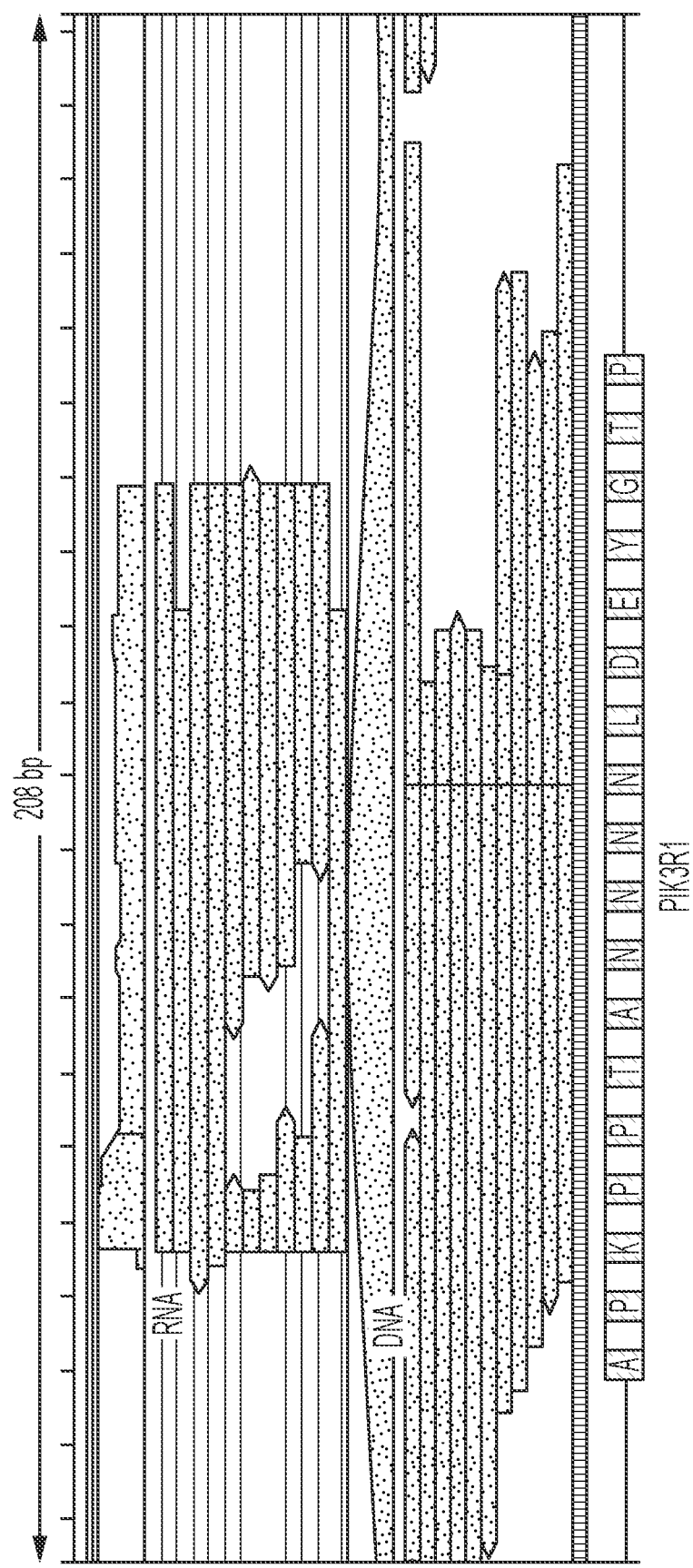
FIG. 9 shows an example of RNA- and DNA-based mutation detection.

Example 7: Detection of RNA- and DNA-based mutation detection in the circulating nucleic acid extracted from a biofluid sample. In this case, PIK3R1 gene M326I mutation detection in DNA and confirmed in RNA (FIG. 9).

Example 8: A case report: AR-V7 and AR mutation detection in the Abiraterone-resistance mCRPC patient plasma.

Figure 10:
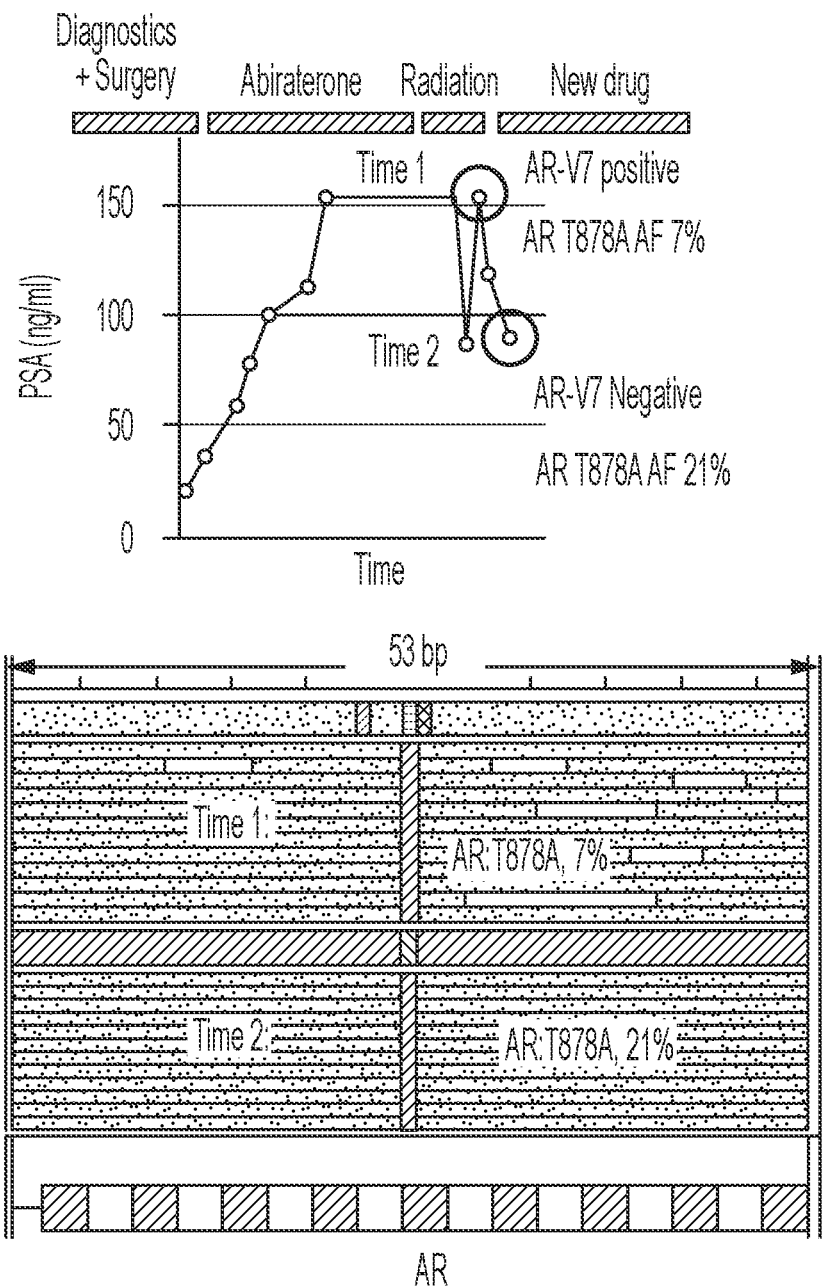
FIG. 10 shows a case report: AR-V7 and AR mutation detection in an Abiraterone-resistance mCRPC patient.

This case is about a prostate cancer patient, who took Abiraterone for a period of time and got drug resistance. At time 1, before taking a new drug, he measured AR-V7 and DNA mutation using our Gene RADAR technology. The NGS data was analyzed by following the workflow shown in FIG. 6. The NGS result shows AR-V7 positive and AR T878A point mutation with 7% mutation allele frequency at time point 1. The new drug aims to suppress the AR expression (including AR-V7 expression). At time point 2, after taking the new drug for about two weeks, he took another measurement. The NGS analysis result shows that AR-V7 was negative and the mutation allele frequency of AR T878A point mutation was increased to 21% (FIG. 10). This result provided very good guidance to the drug treatment.

We claim:

1. A method for detecting a presence or an absence of a genetic alteration from a biofluid sample from a subject, the method comprising:
   (a) obtaining nucleic acids from the biofluid sample;
   (b) separating the nucleic acids into at least a first portion comprising single-stranded ribonucleic acid (ssRNA) molecules and a second portion comprising double-stranded deoxyribonucleic acid (dsDNA) molecules;
   (c) barcoding the ssRNA molecules with a molecular barcode that is unique to each single ssRNA molecule of the ssRNA molecules;
   (d) converting the barcoded ssRNA molecules to barcoded dsDNA molecules;
   (e) mixing the barcoded dsDNA molecules and the dsDNA molecules to produce a nucleic acid mixture;
   (f) sequencing the nucleic acid mixture or derivatives thereof to produce a plurality of sequence reads comprising cell-free RNA (cfRNA)-derived sequence reads from the barcoded dsDNA molecules and cell-free DNA (cfDNA)-derived sequence reads from the dsDNA molecules, wherein each of the cfRNA-derived sequence reads is associated with a molecular barcode;
   (g) aligning the plurality of sequence reads to a reference genome to produce a plurality of aligned sequence reads comprising cfRNA-derived aligned sequence reads and cfDNA-derived aligned sequence reads; and
   (h) detecting the presence or the absence of the genetic alteration based at least in part on an analysis of the plurality of aligned sequence reads and associated molecular barcodes, wherein the detecting comprises using molecular barcodes to distinguish between cfRNA-derived aligned sequence reads and cfDNA-derived aligned sequence reads.

2. The method of claim 1, wherein the barcoded ssRNA molecules are converted to the barcoded dsDNA molecules at least in part by reverse transcribing the barcoded ssRNA molecules to dsDNA after the barcoded ssRNA molecules are ligated to one or more oligonucleotides.

3. The method of claim 1, wherein the genetic alteration is selected from the group consisting of a gene splice variant, a mutation, an insertion or deletion (indel), a copy number change, a fusion, and a combination thereof.

4. The method of claim 1, wherein the biofluid sample is selected from the group consisting of a blood sample, a plasma sample, a serum sample, a urine sample, a sputum sample, a spinal fluid sample, a cerebrospinal fluid sample, a pleural fluid sample, a nipple aspirate sample, a lymph fluid sample, a fluid sample of the respiratory, intestinal, or genitourinary tracts, a tear sample, a saliva sample, a breast milk sample, a fluid sample from a lymphatic system, a semen sample, an intra-organ system fluid sample, an ascitic fluid sample, a tumor cyst fluid sample, an amniotic fluid sample, and a combination thereof.

5. The method of claim 4, wherein the biofluid sample is the plasma sample.

6. The method of claim 4, wherein the biofluid sample is the plasma sample or the urine sample.

7. The method of claim 6, wherein the biofluid sample is the plasma sample.

8. The method of claim 6, wherein the biofluid sample is the urine sample.

9. The method of claim 1, further comprising detecting a presence or an absence of a disease in the subject, based at least in part on the detected presence or absence of the genetic alteration.

10. The method of claim 1, wherein the disease is cancer.

11. The method of claim 10, wherein the cancer is prostate cancer.

12. The method of claim 11, wherein the prostate cancer is castration resistant prostate cancer.

13. The method of claim 1, wherein the genetic alteration occurs in an androgen receptor gene.

14. The method of claim 13, wherein the genetic alteration is an androgen receptor gene splice variant (AR-V) or an androgen receptor (AR) gene mutation.

15. The method of claim 14, wherein the genetic alteration is the AR-V.

16. The method of claim 15, wherein the AR-V is selected from the group consisting of AR-V1, AR-V2, AR-V7, AR-V9, and AR-V567es.

17. The method of claim 14, wherein the genetic alteration is the AR gene mutation.

18. The method of claim 17, wherein the AR gene mutation is selected from the group consisting of AR-FL, AR-T878A, and AR-F876L.

19. The method of claim 1, wherein the converting further comprises extracting RNA molecules from the first portion, and reverse transcribing the extracted RNA molecules to produce complementary DNA molecules.

20. The method of claim 1, wherein obtaining the nucleic acids further comprises extracting both DNA molecules and RNA molecules from the biofluid sample simultaneously, and reverse transcribing the extracted RNA molecules to produce complementary DNA molecules.

* * * * *